US007576105B2

(12) United States Patent
Baxter et al.

(10) Patent No.: US 7,576,105 B2
(45) Date of Patent: Aug. 18, 2009

(54) BENZYL SUBSTITUTED (PIPERIDIN-4-YL)AMINOBENZAMIDO DERIVATIVES

(75) Inventors: Ellen W. Baxter, Glenside, PA (US); Allen B. Reitz, Lansdale, PA (US)

(73) Assignee: Janssen Pharmaceutica, NV, Beerse (BE)

( * ) Notice: Subject to any disclaimer, the term of this patent is extended or adjusted under 35 U.S.C. 154(b) by 400 days.

(21) Appl. No.: 11/314,496

(22) Filed: Dec. 21, 2005

(65) Prior Publication Data

US 2006/0106066 A1    May 18, 2006

Related U.S. Application Data

(63) Continuation of application No. 10/684,991, filed on Oct. 14, 2003, now abandoned.

(60) Provisional application No. 60/418,457, filed on Oct. 15, 2002.

(51) Int. Cl.
*A61K 31/445* (2006.01)
*C07D 211/56* (2006.01)

(52) U.S. Cl. ............... 514/326; 514/329; 546/224; 546/208

(58) Field of Classification Search ............ 514/326, 514/329; 546/224, 208
See application file for complete search history.

(56) References Cited

U.S. PATENT DOCUMENTS 6,130,222 A      10/2000  Roberts et al.
6,436,959 B1 *    8/2002  Carson et al. ............... 514/326

FOREIGN PATENT DOCUMENTS

WO    WO 99/33806 A1    7/1999
WO    WO 02/48112 A2    6/2002
WO    WO 03/020716 A1   3/2003

OTHER PUBLICATIONS

Thomas, James B. et al., "Factors Influencing Agonist Potency Selectivity Opioid Receptor Are Revealed in Structure-Activity Relationship Studies of the 4-[(N-Substituted-4-piperidinyl) arylamino]-N,N-diethylbenzamides", J. Med. Chem., vol. 44, pp. 972-987, 2001.
Podlogar, Brent L. et al., "Synthesis and Evaluation of 4-(N, N-Diarylamino) piperidines with High Selectivity to the -Opioid Receptor: A Combined 3D-QSAR Ligand Docking Study", Drug Design and Discovery, vol. 17, No3. 1, pp. 34-50, 2000.

* cited by examiner

*Primary Examiner*—Rei-tsang Shiao
(74) *Attorney, Agent, or Firm*—John Harbour

(57) ABSTRACT

The present invention is directed to N-benzyl substituted (piperidin-4-yl)aminobenzamido derivatives which are delta-opioid receptor modulators.

22 Claims, No Drawings

BENZYL SUBSTITUTED (PIPERIDIN-4-YL)AMINOBENZAMIDO DERIVATIVES

CROSS REFERENCE TO RELATED APPLICATIONS

This application is a continuation of application Ser. No. 10/684,991, filed Oct. 14, 2003 now abandoned and claims the benefit of provisional application Ser. No. 60/418,457 filed on Oct. 15, 2002. The complete disclosure of each application is hereby incorporated herein by reference for all purposes.

FIELD OF THE INVENTION

The present invention is directed to delta-opioid receptor modulators. More particularly, the present invention is directed to N-benzyl substituted (piperidin-4-yl)aminobenzamido derivatives which are delta-opioid receptor modulators.

BACKGROUND OF THE INVENTION

WO 97/23466 discloses compounds described as having an analgesic effect, having a general and a typical preferred formula:

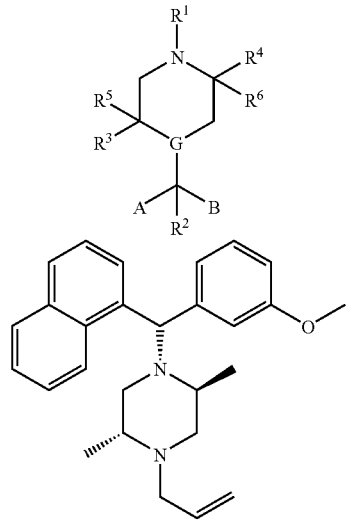

WO 98/28275 further discloses compounds described as having an analgesic effect, having a general and a typical preferred formula:

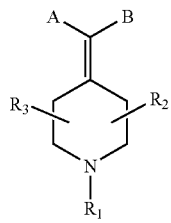

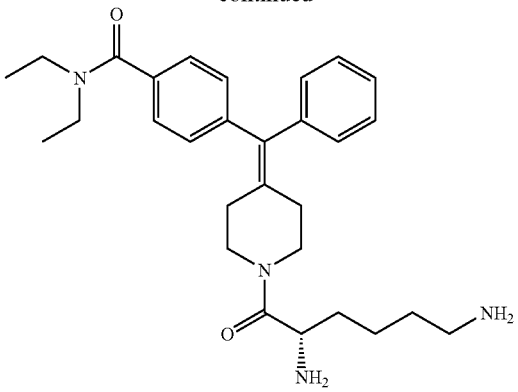

WO 93/15062 discloses compounds which have been described as delta-opioid and mu-opioid receptor agonists, having (approximately) the formula:

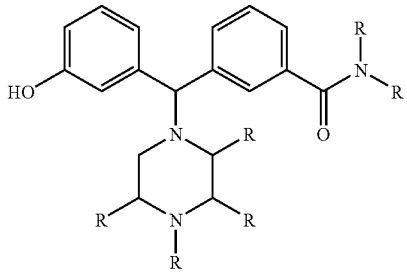

Astra Aktiebolag, World Patent 98/28270 discloses compounds with analgesic activity mediated through the delta opiate receptor having the general formula:

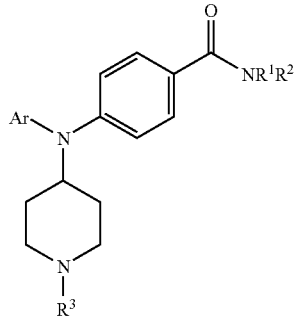

The synthesis and binding affinities for 4-diarylaminotropane compounds of the general formula:

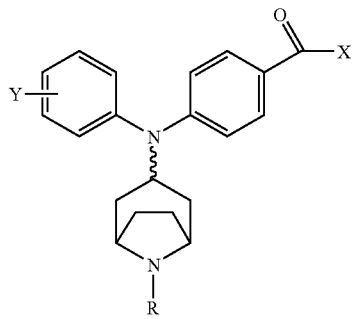

wherein R is hydrogen, methyl, propyl, hexyl, 2-ethylbutyl, allyl, 3,3-dimethallyl, cyclohexylmethyl, phenethyl, phenyl-propyl, 2,2-diphenylethyl, 3,4-dimethoxyphenethyl, 4-fluorophenethyl, 2-furylmethyl; 3,4-methylenedioxybenzyl, cyano and X is N,N-dimethylamino, N,N-diethylamino, N,N-dipropylamino, N-methyl, N-ethylamino, N-methyl, N-propylamino, N-methyl, N-phenylamino, N-ethyl, N-(4-methyl)benzylamino, N-butyl, N-ethylamino, N-butyl, N-propylamino, [N-ethyl, N-(2-methyl)allyl]amino, hydroxy, O-t-butyl and 1-pyrrolidinyl; and, Y is hydrogen, methoxy and methylthio as δ-opioid agonists have been described (Boyd, R. E., Carson, J. R., Codd, E. E., Gauthier, A. D., Neilson, L. A and Zhang, S-P., *Biorg. Med. Chem. Lett.*, 2000, 10: 1109-1111).

The 4-[aryl(8-azabicyclo[3.2.1]octan-3-yl)]aminobenzoic acid derivatives disclosed in the above reference are claimed as δ-opioid receptor modulators in World Patent 01/46191.

4-[(8-Alkyl-8-azabicyclo[3.2.1]octyl-3-yl)-3-arylanilino]-N,N-diethylbenzamides have also been described as selective δ-opioid ligands (Thomas, J. B., Atkinson, R. N., Rothman, R. B., Burgess, J. P., Mascarella, S. W., Dersch, C. M., Xu, H. and Carroll, F. I., *Biorg. Med. Chem. Lett.*, 2000, 10: 1281-1284).

In addition, 3-(diarylmethylene)-8-azabicyclo[3.2.1]octanes are described as δ- and μ-receptor modulators in World Patent 01/66543.

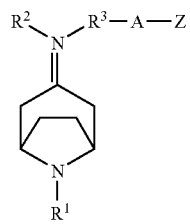

N,N-Diaryl piperazinebenzamides have also been reported to be selective δ-opioid ligands (Nortey, S. O.; Baxter, E. W.; Codd, E. E.; Zhang, S.-P.; Reitz, A. B. *Biorg. Med. Chem. Lett.*, 2001, 11: 1741-1743). A representative structure is illustrated below:

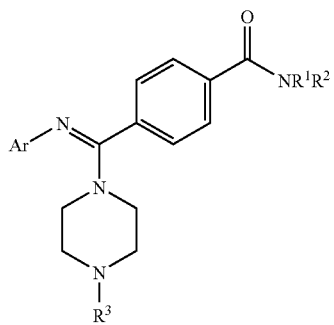

The foregoing reference compounds have been described as either delta- or mu-opioid receptor agonists or antagonists.

It is an object of the present invention to provide substituted (piperidin-4-yl)aminobenzamido compounds which are delta-opioid receptor modulators. It is also an object of the present invention to provide substituted (piperidin-4-yl)aminobenzamido compounds which are δ-opioid receptor agonists useful as analgesics. It is another object of the present invention to provide δ-opioid receptor antagonists useful for treating immune disorders, inflammation, neurological conditions, psychiatric conditions, drug abuse, alcohol abuse, gastritis, diarrhea, cardiovascular disorders or respiratory disorders. It is a further object of the present invention to provide a method for treating a disorder modulated by the δ-opioid receptor.

SUMMARY OF THE INVENTION

The present invention provides delta-opioid receptor modulators of Formula (I):

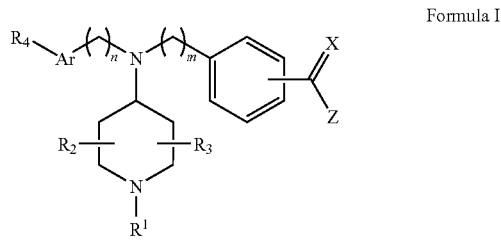

Formula I wherein:

Ar is selected from the group consisting of aryl and heteroaryl;

m is an integer from 0 to 2, n is an integer from 0 to 2, with the proviso that m and n are not both simultaneously 0;

$R_1$ is selected from the group consisting of hydrogen, $C_{1-8}$alkyl, $C_{2-8}$alkenyl, aryl, aryl($C_{1-8}$)alkyl, heteroaryl ($C_{1-8}$)alkyl, amino($C_{1-8}$)alkyl, $C_{1-8}$alkyl-NH—($C_{1-8}$)alkyl, ($C_{1-8}$alkyl)$_2$-N—($C_{1-8}$)alkyl, hydroxy($C_{1-8}$)alkyl and $C_{1-8}$alkoxy($C_{1-8}$)alkyl;

$R_2$ and $R_3$ are optionally present and independently selected from $C_{1-8}$alkyl;

$R_4$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkyloxy, $C_{1-8}$alkylthio, trifluoro($C_{1-8}$) alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$) alkylaryl, —N[($C_{1-8}$)alkylaryl]$_2$, —CO$_2$H, —CO$_2$($C_{1-8}$) alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —S(O$_2$)NH$_2$, —S(O$_2$)NH($C_{1-8}$)alkyl, —S(O$_2$)N[($C_{1-8}$)alkyl]$_2$, —C(O)($C_{1-8}$)alkyl, —C(O)aryl, —C(O)($C_{1-8}$)alkylaryl, aryl, heteroaryl, heterocyclyl, halogen, hydroxy, cyano, and nitro;

X is selected from the group consisting of O and S;

Z is N($R_5$)($R_6$) or is a 5- or 6-membered saturated, monocyclic, heterocyclic ring, wherein said heterocyclic ring contains one nitrogen member which is the point of attachment, optionally contains one additional heteroatom member of oxygen, sulfur or nitrogen and optionally contains a double bond between two ring members;

$R_5$ and $R_6$ are independently selected from the group consisting of hydrogen, $C_{1-8}$alkyl, hydroxy($C_{1-8}$)alkyl, $C_{2-8}$alkenyl, $C_{3-8}$cycloalkyl, aryl and aryl($C_{1-8}$)alkyl, wherein said cycloalkyl, aryl and the aryl portion of aryl($C_{1-8}$)alkyl are optionally substituted with one to three substituents independently selected from the group consisting of $C_{1-8}$alkyl, $C_{2-8}$alkenyl, $C_{1-8}$alkoxy, trifluoro($C_{1-8}$)alkyl, trifluoro($C_{1-8}$)alkoxy, $C_{3-8}$cycloalkyl and halogen; and, the moiety —C(X)Z is attached on the phenyl at the 3 or 4 position;

and pharmaceutically acceptable enantiomers, diastereomers and salts thereof.

DETAILED DESCRIPTION OF THE INVENTION

Embodiments of the present invention include compounds selected from a compound of Formula (I) wherein, preferably, Ar is phenyl, naphthyl, furyl, thienyl, oxazolyl, thiazolyl, imidazolyl, isozazolyl, isothiazolyl, indolyl, indazolyl, benzo[b]thienyl, quinolinyl, isoquinolinyl, quinazolinyl, pyrrolyl, imidazolyl, pyrazolyl, pyridinyl, pyrimidinyl, pyrazinyl, or pyridazinyl.

More preferably, Ar is phenyl or pyridinyl.

Embodiments of the present invention include compounds selected from a compound of Formula (I) wherein, preferably, m is an integer from 0 to 1, n is an integer from 0 to 1, with the proviso that m and n are not both simultaneously 0.

Embodiments of the present invention include compounds selected from a compound of Formula (I) wherein, preferably, $R_1$ is selected from the group consisting of hydrogen, $C_{1-4}$alkyl, $C_{2-4}$alkenyl, aryl, aryl($C_{1-4}$)alkyl, heteroaryl($C_{1-4}$)alkyl, $NH_2(C_{1-14})$alkyl, $C_{1-4}$alkyl-NH—($C_{1-4}$)alkyl, ($C_{1-4}$alkyl)$_2$-N—($C_{1-4}$)alkyl, hydroxy($C_{1-4}$)alkyl and $C_{1-4}$alkoxy($C_{1-4}$)alkyl;

More preferably, $R_1$ is selected from the group consisting of hydrogen, $C_{1-4}$alkyl and $C_{2-4}$alkenyl.

Most preferably, $R_1$ is selected from the group consisting of hydrogen, n-propyl and allyl.

Embodiments of the present invention include compounds selected from a compound of Formula (I) wherein, preferably, $R_2$ and $R_3$ are optionally present and independently selected from $C_{1-4}$alkyl.

More preferably, $R_2$ and $R_3$ are not present.

Embodiments of the present invention include compounds selected from a compound of Formula (I) wherein, preferably, $R_4$ is one to three substituents.

Preferably, $R_4$ is independently selected from the group consisting of hydrogen, $C_{1-8}$alkyl, $C_{1-8}$alkoxy, trifluoro($C_{1-8}$)alkyl, trifluoro($C_{1-8}$)alkoxy, cyano, halogen, hydroxy and nitro.

More preferably, $R_4$ is independently selected from the group consisting of hydrogen, $C_{1-8}$alkoxy, trifluoro($C_{1-8}$)alkyl, hydroxy and halogen.

Most preferably, $R_4$ is independently selected from the group consisting of hydrogen, methoxy, trifluoromethyl, hydroxy, fluoro and chloro.

Embodiments of the present invention include compounds selected from a compound of Formula (I) wherein, preferably, X is O.

Embodiments of the present invention include compounds selected from compounds of Formula (I) wherein, preferably, Z is $N(R_5)(R_6)$.

Embodiments of the present invention include those compounds selected from compounds of Formula (I) wherein, preferably, $R_5$ and $R_6$ are independently selected from the group consisting of hydrogen, $C_{1-4}$alkyl, hydroxy($C_{1-4}$)alkyl, $C_{2-4}$alkenyl, $C_{3-8}$cycloalkyl, aryl and aryl($C_{1-4}$)alkyl, wherein said cycloalkyl, aryl and the aryl portion of aryl($C_{1-8}$)alkyl are optionally substituted with one to three substituents independently selected from the group consisting of $C_{1-4}$alkyl, $C_{2-4}$alkenyl, $C_{1-4}$alkoxy, $C_{3-8}$cycloalkyl, halogen, trifluoro($C_{1-4}$)alkyl and trifluoro($C_{1-4}$)alkoxy;

More preferably, $R_5$ and $R_6$ are independently selected from the group consisting of hydrogen and $C_{1-4}$alkyl.

Most preferably, $R_5$ and $R_6$ independently selected from the group consisting of hydrogen, methyl and ethyl.

Exemplified compounds of the present invention include compounds of Formula (Ia):

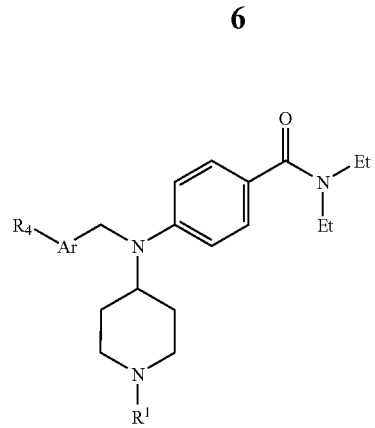

Formula (Ia)

Wherein Ar $R_1$ and $R_4$ are dependently selected from:

| Compound | $R_1$ | Ar | $R_4$ |
|---|---|---|---|
| 1 | n-Pr | phenyl | 3-methoxy |
| 2 | n-Pr | phenyl | 3-hydroxy |
| 3 | n-Pr | phenyl | 3-chloro |
| 4 | n-Pr | phenyl | 2-methoxy |
| 5 | n-Pr | phenyl | 2-hydroxy |
| 6 | n-Pr | phenyl | 3-fluoro |
| 7 | n-Pr | phenyl | H |
| 8 | H | phenyl | H |
| 9 | allyl | phenyl | H |
| 10 | i-Pr | phenyl | H |
| 11 | N,N-dimethyl aminopropyl | phenyl | H |
| 12 | n-Pr | phenyl | 4-methoxy |
| 13 | n-Pr | 3-pyridinyl | H |
| 14 | Me | phenyl | H |
| 15 | n-Pr | phenyl | 3-trifluoromethyl |
| 16 | n-Pr | phenyl | 4-fluoro | and pharmaceutically acceptable salts thereof.

Exemplified compounds of the present invention also include compounds of Formula (Ib):

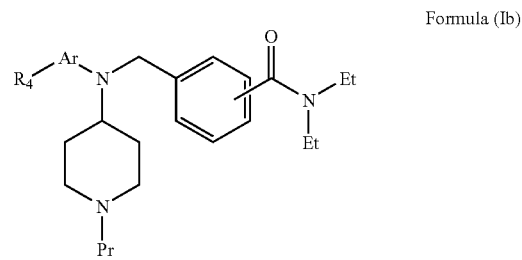

Formula (Ib)

Wherein Ar, $R_4$ and the position for —C(O)(NEt$_2$) is selected from:

| Compound | Ar | $R_4$ | Amide Substitution |
|---|---|---|---|
| 17 | phenyl | 3-methoxy | 4 |
| 18 | phenyl | 3-methoxy | 3 |
| 19 | phenyl | 3-hydroxy | 3 |
| 20 | phenyl | H | 3 |
| 21 | phenyl | 3-fluoro | 3 | and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201-217; *J. Pharm. Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

Where the compounds according to this invention are chiral, they may accordingly exist as enantiomers. In addition, the compounds may exist as diastereomers. It is to be understood that all such stereoisomers and racemic mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

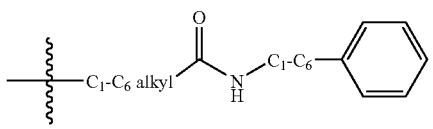

The terms used in describing the invention are commonly used and known to those skilled in the art. However, the terms that could have other meanings are hereinafter defined. These definitions apply to the terms as they are used throughout this specification, unless otherwise limited in specific instances, either individually or as part of a larger group.

An "independently" selected substituent refers to a group of substituents, wherein the substituents may be different. Therefore, designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, the term "alkyl" refers to a saturated straight or branched chain consisting solely of 1-8 hydrogen substituted carbon atoms; preferably, 1-6 hydrogen substituted carbon atoms; and, most preferably, 1-4 hydrogen substituted carbon atoms. The term "alkenyl" refers to a partially unsaturated straight or branched chain consisting solely of 2-8 hydrogen substituted carbon atoms that contains at least one double bond. The term "alkynyl" refers to a partially unsaturated straight or branched chain consisting solely of 2-8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl, alkenyl and alkynyl chains are optionally substituted within the alkyl chain or on a terminal carbon atom.

The term "cycloalkyl" refers to a saturated or partially unsaturated monocyclic alkyl ring consisting of 3-8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated monocyclic ring having five or six members of which at least one member is a N atom and which optionally contains one additional O or S atom or one, two or three additional N atoms.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl, phenanthracenyl or anthracenyl.

The term "heteroaryl" refers to an aromatic monocyclic ring system containing five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms or an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]thienyl, quinolinyl, isoquinolinyl or quinazolinyl.

Whenever the term "alkyl" or "aryl" or either of their prefix roots appear in a name of a substituent (e.g., aryl($C_{1-6}$)alkyl) it shall be interpreted as including those limitations given above for "alkyl" and "aryl." Designated numbers of carbon atoms (e.g., $C_{1-6}$) shall refer independently to the number of carbon atoms in an alkyl or cycloalkyl moiety or to the alkyl portion of a larger substituent in which alkyl appears as its prefix root.

The term "halogen" shall include iodine, bromine, chlorine and fluorine.

The novel substituted benzamido compounds of the present invention are useful δ-opioid receptor modulators. In particular, the instant substituted benzamido compounds are δ-opioid receptor agonists useful as analgesics. Examples of pain intended to be within the scope of the present invention include, but are not limited to, centrally mediated pain, peripherally mediated pain, structural or soft tissue injury related pain, progressive disease related pain, neuropathic pain and acute pain such as caused by acute injury, trauma or surgery and chronic pain such as caused by neuropathic pain conditions, diabetic peripheral neuropathy, post-herpetic neuralgia, trigeminal neuralgia, post-stroke pain syndromes or cluster or migraine headaches. The utility of the instant compounds as δ-opioid receptor agonists can be determined according to the procedures described herein.

Alternatively, the compounds of the present invention may be δ-opioid receptor antagonists useful as immunosuppressants, antiinflammatory agents, agents for the treatment of neurological and psychiatric conditions, medicaments for drug and alcohol abuse, agents for treating gastritis and diarrhea, cardiovascular agents and agents for the treatment of respiratory diseases, having reduced side-effects. The utility of the instant compounds as δ-opioid receptor antagonists can be determined by those skilled in the art using established animal models.

An embodiment of the invention is a pharmaceutical composition comprising one or more compounds of this invention in association with a pharmaceutically acceptable carrier. Another embodiment is a pharmaceutical composition made by mixing any of the compounds described above and a pharmaceutically acceptable carrier. A further embodiment is a process for making a pharmaceutical composition comprising mixing any of the compounds described above and a pharmaceutically acceptable carrier.

The present invention includes a method for treating a disorder modulated by the δ-opioid receptor. An embodiment of the present invention is a method for treating pain modulated by a δ-opioid agonist. Another embodiment is a method for treating immune disorders, inflammation, neurological conditions, psychiatric conditions, drug abuse, alcohol abuse, gastritis, diarrhea, cardiovascular disorders or respiratory disorders modulated by a δ-opioid antagonist.

The present invention therefore provides a method for the use of the instant substituted benzamido compounds as δ-opioid receptor modulators comprising administering to a subject any of the compounds as defined herein in a therapeutically effective amount. A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

A therapeutically effective amount for use of the instant compounds or a pharmaceutical composition thereof comprises a dose range of from about 0.001 mg to about 12,000 mg, in particular from about 0.1 mg to about 4000 mg or, more particularly from about 1 mg to about 2000 mg of active ingredient per day for an average (70 kg) human.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. Advantageously, compounds of the present invention may be administered in a single daily dose or the total daily dosage may be administered in divided doses of two, three or four times daily.

It is apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

Compounds of this invention may be administered in any of the foregoing compositions and dosage regimens or by means of those compositions and dosage regimens established in the art whenever use of the compounds of the invention as δ-opioid receptor modulators is required for a subject in need thereof.

The terms used in describing the invention are commonly used and known to those skilled in the art. As used herein, the following abbreviations have the indicated meanings:

| Cpd | Compound |
| --- | --- |
| BINAP | 2,2'-Bis(diphenylphosphino)-1,1'-binaphthyl |
| h | Hour |
| min | Minute |
| Pd$_2$dba$_3$ | Tris(dibenzylideneacetone)-dipalladium(0) |
| rt | Room temperature |
| Tris | Tris(hydroxymethyl)aminomethane |

General Synthetic Methods

Representative compounds of the present invention can be synthesized in accordance with the general synthetic methods described below and are illustrated in the schemes that follows. Since the schemes are an illustration, the invention should not be construed as being limited by the chemical reactions and conditions expressed. The preparation of the various starting materials used in the schemes is well within the skill of persons versed in the art.

Scheme A

As described below in Scheme A, certain target benzoic acid derivative compounds of the invention were prepared using synthetic methods whereby a 1-substituted 4-piperidone A1 was condensed with an appropriately substituted benzyl amine or heteroarylmethyl amine under reductive amination conditions to provide aminopiperidine A2. Sodium triacetoxyborohydride was the reagent of choice. Such reactions were typically conducted with an equivalent of acid, such as acetic acid, in an aprotic solvent, preferably dichloromethane, 1,2-dichloroethane, or tetrahydrofuran. Alternative reaction conditions include sodium cyanoborohydride in methanol with an equivalent of acid or sodium borohydride in methanol. Compound A2 was then reacted with bromobenzamide A3, prepared by condensation of the corresponding acid chloride with an appropriate amine, in the presence of a palladium catalyst and a catalytic amount of BINAP with sodium tert-butoxide in refluxing toluene to provide target A4. When Ar is methoxy substituted phenyl, phenolic compounds may be obtained by deprotecting the methoxy with boron tribromide.

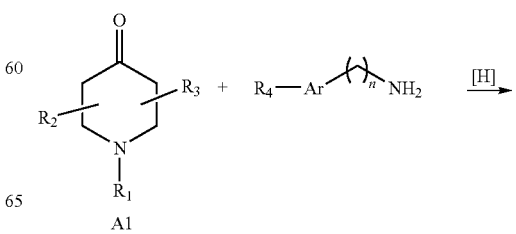

A1

-continued

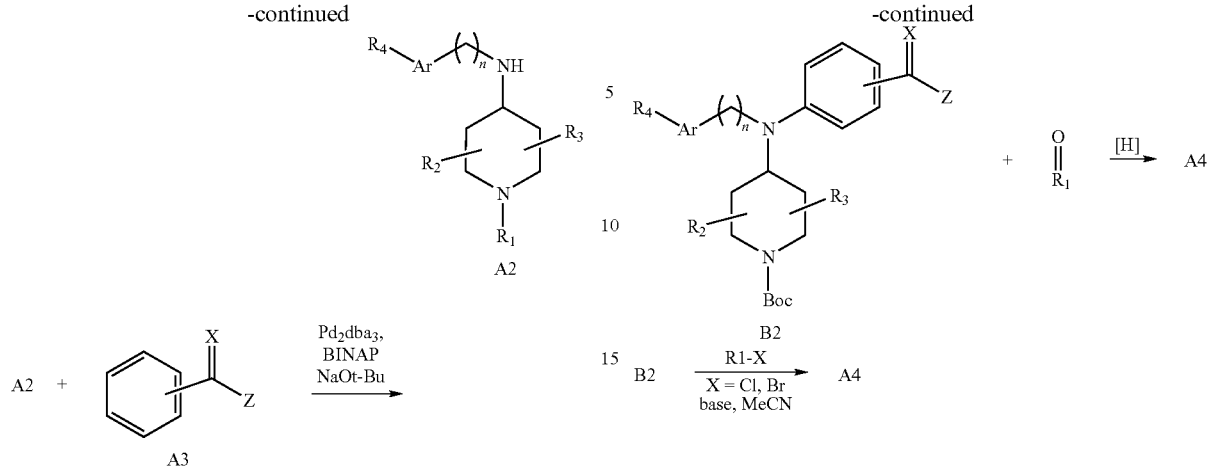

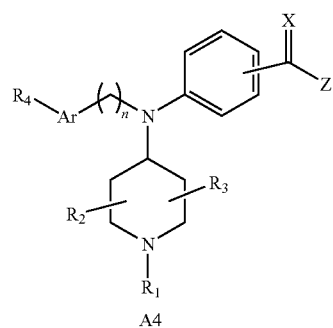

Scheme B

As described below in Scheme B, certain target benzoic acid derivative compounds of the invention were prepared using synthetic methods whereby a 1-tert-butoxycarbonyl-4-aminopiperidine B1 was treated with acid to give the corresponding 1-unsubstituted 4-aminopiperidine B2. This material was then reacted with an aldehyde or ketone generally represented as B3 using the reductive alkylation conditions described for Scheme A which yielded targets A4. Alternatively, compound B2 was reacted with an alkyl chloride or bromide in refluxing acetonitrile in the presence of a base such as potassium carbonate or triethylamine to yield targets A4. A catalytic amount of sodium iodide can be added to facilitate the reaction.

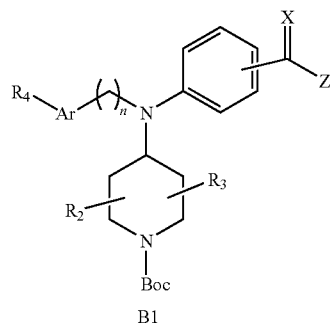

-continued

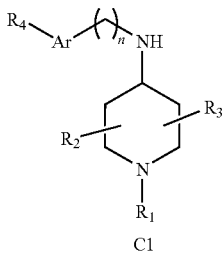

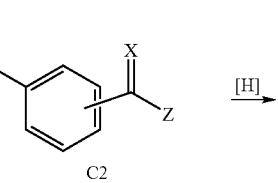

Scheme C

As described below in Scheme C, certain compounds of the invention were prepared using synthetic methods whereby a 1-substituted 4-piperidone A1 was condensed with an appropriately substituted aromatic amine under reductive amination conditions to provide aminopiperidine C1 using the conditions described for procedure A. Intermediate C1 was then subjected to a second reductive alkylation using a formyl substituted benzamide C2 which was made by condensation of a formyl benzoic acid with a secondary amine with a coupling reagent such as carbonyl diimidazole to provide targets C3.

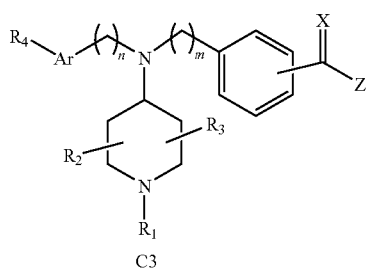

Scheme D

As described below in Scheme D, certain compounds of the invention were prepared using synthetic methods whereby an N-tert-butoxycarbonylaminomethylbenzoic acid derivative D1 was condensed with an amine D2 as described in Scheme C to provide amide D3. After deprotection, the resulting amine D4 was reacted with a 1-substituted-4-piperidone using the reductive alkylation conditions described in Scheme A to afford aminopiperidine D5. Treatment of D5 with an appropriate aryl halide under the reaction conditions described in Scheme A yielded targets D6.

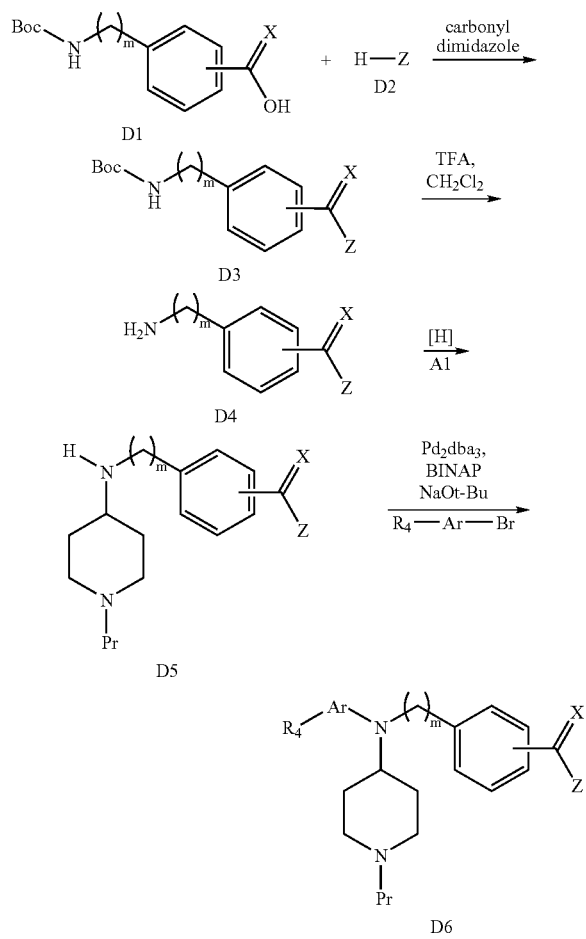

Specific Synthetic Methods

Specific compounds which are representative of the invention may be prepared as per the following examples offered by way of illustration and not by way of limitation. No attempt has been made to optimize the yields obtained in any of the reactions. One skilled in the art would know how to increase such yields through routine variations in reaction times, temperatures, solvents and/or reagents.

Example 1

N,N-Diethyl-4-[benzyl(1-propylpiperidin-4-yl)amino]benzamide (Compound 7)

To a solution of 1-propyl-4-piperidone (10.0 g, 70.8 mmol), benzylamine (9.7 g, 70.8 mmol), and acetic acid (4.25 g, 70.8 mmol) in 200 mL of dry dichloromethane was added sodium triacetoxyborohydride (30.0 g, 142 mmol) under nitrogen. The mixture was stirred for 20 h, and then aqueous 1 N NaOH (200 mL) solution was added. After 1 h of stirring, the layers were separated, and the aqueous layer was extracted twice with dichloromethane (100 mL). The organic extracts were combined, washed twice with 1 N NaOH (100 mL), dried ($Na_2SO_4$), and concentrated to give 11.26 g of a yellow oil. This material was purified on flash silica gel (chloroform to 20% methanol-chloroform) to provide the acetate salt of the desired product as 7.43 g of a cream-colored solid. This material was dissolved in dichloromethane (200 mL), washed three times with 1 N NaOH (100 mL), dried ($Na_2SO_4$), and concentrated to give 6.16 g of a yellow oil. Subsequently, 4.47 g of this material was repurified by flash silica gel chromatography (10% methanol-chloroform to 20% methanol-chloroform) to provide 3.47 g of N-benzyl-1-propyl-4-piperidinamine as a yellow oil. MS (ES), m/z 233 ($MH^+$). 300 MHz $^1$H NMR ($CDCl_3$) δ0.88 (t, J=7.3 Hz, 3H), 1.37-1.59 (m, 4H), 1.82-2.02 (m, 4H), 2.25 (dd, J=9.1, 6.5 Hz, 2H), 2.43-2.56 (m, 1H), 2.87 (br d, J=11.9 Hz, 2H), 3.82 (s, 2H), 7.17-7.36 (m, 5H).

A solution of N-benzyl-1-propyl-4-piperidinamine (3.47 g, 14.9 mmol), N,N-diethyl-4-bromobenzamide (3.82 g, 14.9 mmol), $Pd_2$ $dba_3$ (0.14 g, 0.149 mmol), (+)-BINAP (0.28 g, 0.448 mmol) and sodium t-butoxide (2.00 g, 20.9 mmol) in 18.5 mL of dry toluene was heated at 120° C. under Argon in a pressure vessel for 46 h. The mixture was cooled, and dichloromethane (75 mL) and water (75 mL) were added to the reaction flask. The layers were separated, and the aqueous layer was extracted twice with dichloromethane (75 mL). The organic layers were combined and washed with brine (75 mL) and dried ($Na_2SO_4$). Evaporation of the solvent afforded a dark brown oil with some solid particles evident. This material was purified on a flash silica gel column (5% methanol-chloroform to 10% methanol-chloroform) to provide 3.75 g (62% yield) of N,N-diethyl-4-[benzyl(1-propylpiperidin-4-yl)amino]benzamide as a golden-brown oil. This material was dissolved in acetonitrile, and oxalic acid (0.82 g) was added. Upon addition of diethyl ether, a cream-colored precipitate came out of solution. Recrystallization from acetonitrile and diethyl ether afforded 2.41 g (32% yield) of a cream-colored solid, mp 92-99° C. MS (ES), m/z 408 ($MH^+$). 300 MHz $^1$H NMR (DMSO-$d_6$) δ0.89 (t, J=7.3 Hz, 3H), 1.08 (t, J=7.0 Hz, 6H), 1.56-1.73 (m, 2H), 1.82-2.10 (m, 4H), 2.94 (brt, J=7.8 Hz, 2H), 3.08 (br t, 2H), 3.31 (dd, J=6.9 Hz, 2H), 3.46 (br d, J=11.5 Hz, 2H), 4.18-4.35 (br m, 1H), 4.49 (br s, 2H), 6.74 (d, J=8.7 Hz, 2H), 7.20-7.35 (m, 7H). Elemental analysis: Calculated for $C_{26}H_{37}N_3O.C_2H_2O_4.0.6H_2O$: C, 66.14; H, 7.97; N, 8.26. Found C, 65.90; H, 7.78; N, 8.01.

Using the procedure of Example 1 and the appropriate reagents, starting materials and purification methods known to those skilled in the art, other compounds of the present invention may be prepared including, but not limited to:

| Cpd | Name | ES-MS m/z ($MH^+$) |
|---|---|---|
| 1 | N,N-diethyl-4-[3-methoxybenzyl(1-propylpiperidin-4-yl)amino]benzamide | 438 |
| 3 | N,N-diethyl-4-[3-chlorobenzyl(1-propylpiperidin-4-yl)amino]benzamide | 442 |
| 4 | N,N-diethyl-4-[2-methoxybenzyl(1-propylpiperidin-4-yl)amino]benzamide | 438 |
| 6 | N,N-diethyl-4-[3-fluorobenzyl(1-propylpiperidin-4-yl)amino]benzamide | 438 |
| 12 | N,N-diethyl-4-[3-fluorobenzyl(1-propylpiperidin-4-yl)amino]benzamide | 426 |

-continued

| Cpd | Name | ES-MS m/z (MH+) |
|---|---|---|
| 13 | N,N-diethyl-4-[3-pyridylmethyl(1-propylpiperidin-4-yl)amino]benzamide | 409 |
| 15 | N,N-diethyl-4-[3-trifluoromethylphenyl(1-propylpiperidin-4-yl)amino]benzamide | 476 |
| 16 | N,N-diethyl-4-[4-fluoromethylphenyl(1-propylpiperidin-4-yl)amino]benzamide | 426 |

Example 2

N,N-Diethyl-4-[3-hydroxybenzyl(1-propylpiperidin-4-yl)amino]benzamide (Compound 2)

A solution of N,N-diethyl-4-[3-methoxybenzyl(1-propylpiperidin-4-yl)amino]benzamide (Compound 1) in 20 mL of dry dichloromethane was cooled to −78° C. under Argon. A solution of boron tribromide (6.44 mL, 6.44 mmol, 1.0 M) in dichloromethane was added dropwise. The reaction mixture was allowed to warm to ambient temperature overnight. After 21 h of stirring, the reaction mixture was poured into saturated aqueous sodium bicarbonate solution (30 mL). The layers were separated, and the aqueous solution was extracted twice (30 mL) with dichloromethane. The organic extracts were combined and dried ($Na_2SO_4$). Evaporation of the solvent afforded a yellow-brown glass. This material was suspended in 50 mL of saturated aqueous sodium carbonate solution and refluxed 20 h. After cooling, the reaction mixture was poured into a separatory funnel and extracted three times with chloroform. The organic extracts were combined and dried ($Na_2SO_4$). Evaporation of the solvent afforded a brown foam. This material was purified by preparative thin layer chromatography on two 20 cm×20 cm tapered silica gel plates with 3% methanol-chloroform. After three solvent runs, 0.04 g (9%) of N,N-diethyl-4-[3-hydroxybenzyl(1-propylpiperidin-4-yl)amino]benzamide was obtained as a yellow solid. MS (ES), m/z 424 (MH+). 300 MHz $^1$H NMR ($CDCl_3$) δ0.89 (t, J=7.3 Hz, 3H), 1.18 (t, J=7.0 Hz, 6H), 1.43-1.61 (m, 2H), 1.67-1.88 (m, 4H), 1.95-2.14 (m, 2H), 2.28-2.39 (m, 2H), 3.01 (br d, J=11.3 Hz, 2H), 3.26-3.54 (br m, 2H), 3.69-3.86 (br m, 1H), 4.37 (br s, 2H), 6.52-6.66 (m, 4H), 6.70 (d, J=7.6 Hz, 1H), 7.12 (t, J=7.7 Hz, 1H), 7.16-7.29 (m, 2H).

Example 3

N,N-Diethyl-4-[2-hydroxybenzyl(1-propylpiperidin-4-yl)amino]benzamide (Compound 5)

Following the procedure of Examples 1 and 2, N,N-diethyl-4-[2-hydroxybenzyl(1-propylpiperidin-4-yl)amino]benzamide was obtained as a beige powder. MS (ES), m/z 424 (MH+). 300 MHz $^1$H NMR ($CDCl_3$) δ0.91 (t, J=7.3 Hz, 3H), 1.17 (t, J=7.0 Hz, 6H), 1.51-1.70 (m, 2H), 1.75-2.00 (m, 4H), 2.06-2.22 (m, 2H), 2.34-2.48 (m, 2H), 3.15 (br d, 2H), 3.25-3.55 (br m, 4H), 3.60-3.85 (br m, 1H), 4.43 (br s, 2H), 6.57 (d, J=7.7 Hz, 1H), 6.66-6.85 (m, 3H), 6.98-7.12 (m, 2H), 7.19-7.30 (m, 1H).

Example 4

N,N-Diethyl-4-[benzyl(piperidin-4-yl)amino]benzamide (Compound 8)

To a solution of 1-(tert-butoxycarbonyl)-4-piperidone (10.0 g, 50.2 mmol), benzylamine (5.4 g, 50.2 mmol), and acetic acid (3.01 g, 50.2 mmol) in 200 mL of dry dichloromethane was added sodium triacetoxyborohydride (21.2 g, 100 mmol) under nitrogen. The mixture was stirred for three days, and then aqueous 1 N NaOH (200 mL) solution was added. After 1 h of stirring, the layers were separated, and the aqueous layer was extracted twice with dichloromethane (100 mL). The organic extracts were combined, washed twice with 1 N NaOH (100 mL), dried ($Na_2SO_4$), and concentrated to give 13.46 g of 4-benzylamino-1-(tert-butoxycarbonyl)piperidine as a cream-colored waxy solid. MS (ES), m/z 291 (MH+). 300 MHz $^1$H NMR ($CDCl_3$) δ1.22-1.39 (br q, 2H), 1.45 (s, 9H), 1.86 (br d, J=11.3 Hz, 2H), 2.60-2.93 (m, 4H), 3.82 (s, 2H), 3.85-4.20 (br m, 2H), 7.19-7.37 (m, 5H).

A solution of 4-benzylamino-1-(tert-butoxycarbonyl)piperidine (2.63 g, 9.06 mmol), N,N-diethyl-4-bromobenzamide (2.32 g, 9.06 mmol), $Pd_2dba_3$ (0.08 g, 0.091 mmol), (+)-BINAP (0.17 g, 0.272 mmol) and sodium t-butoxide (1.22 g, 12.7 mmol) in 18 mL of dry toluene was heated at 120° C. under Argon in a pressure vessel for 48 h. The mixture was cooled, and dichloromethane (75 mL) and water (75 mL) were added to the reaction flask. The layers were separated, and the aqueous layer was extracted twice with dichloromethane (75 mL). The organic layers were combined and washed with brine (75 mL) and dried ($Na_2SO_4$). Evaporation of the solvent afforded a dark brown semi-solid. This material was purified on a flash silica gel column (5% methanol-chloroform) to provide 2.79 g of impure product. This material was repurified on a flash silica gel column (5% methanol-chloroform) to give 1.11 g of N,N-diethyl-4-[phenyl(1-(tert-butoxycarbonyl)piperidin-4-yl)amino]benzamide as a golden-brown semisolid. MS (ES), m/z 466 (MH+). 300 MHz $^1$H NMR ($CDCl_3$) δ1.02-1.33 (br m, 6H), 1.17 (t, J=7.0 Hz, 3H), 1.45 (s, 9H), 11.50-1.69 (br q, 2H), 1.85 (br d, J=12.1 Hz, 2H), 2.81 (br t, J=12.3 Hz, 2H), 3.16-3.34 (br m, 2H), 3.32-3.48 (br q, 2H), 3.47-3.62 (br m, 2H), 3.88-4.02 (br m, 1H), 4.02-4.38 (br m, 2H), 4.48 (br s, 2H), 6.67 (d, J=8.8 Hz, 2H), 7.14-7.29 (m, 4H), 7.32-7.40 (m, 3H).

To a solution of N,N-diethyl 3-(N-tert-butoxycarbonylmethylamino)benzamide (1.11 g, 2.38 mmol) in 34 mL of dichloromethane was added 24 mL of trifluoroacetic acid. After 20 h of stirring, the reaction mixture was diluted with 135 mL of dichloromethane. Then, the reaction mixture was slowly added to an ice-cooled solution of 1N NaOH solution (200 mL). The layers were separated, and the aqueous layer was extracted three times with dichloromethane (75 mL). The organic extracts were combined, washed with brine (150 mL), dried ($Na_2SO_4$), and concentrated to give 0.74 g (85%) of N,N-diethyl-4-[phenyl(piperidin-4-yl)amino]benzamide as a yellow glass. MS (ES), m/z 366 (MH+). 300 MHz $^1$H NMR ($CDCl_3$) δ1.06-1.32 (m, 6H), 1.65-1.82 (br qd, 2H), 1.88 (br d, J=11.2 Hz, 2H), 2.79 (br t, J=11.5 Hz, 2H), 3.21 (br d, J=12.1 Hz, 2H), 3.42 (br d, J=6.5 Hz, 2H), 3.59-3.86 (br s, 1H), 3.85-4.02 (br m, 1H), 4.51 (br s, 2H), 6.66 (d, J=8.7 Hz, 2H), 7.10-7.35 (m, 7H).

Example 5

N,N-Diethyl-4-[benzyl(1-allylpiperidin-4-yl)amino]benzamide (Compound 9)

To a solution of N,N-diethyl-4-[benzyl(piperidin-4-yl)amino]benzamide (Compound 8) (0.25 g, 0.684 mmole) in 10 mL of acetonitrile was added potassium carbonate (0.10 g, 0.752 mmole) and allyl bromide (0.08 g, 0.684 mmol). The reaction mixture was stirred for six days under Argon and then was diluted with water (50 mL). This solution was extracted three times with dichloromethane (50 mL). The organic extracts were combined, washed with sodium carbonate solution, dried (Na$_2$SO$_4$), and concentrated to provide a yellow foam. This material was purified on a flash silica gel column (5% methanol-chloroform to 10% methanol-chloroform) to provide 0.11 g (40%) of N,N-diethyl-4-[benzyl(1-allylpiperidin-4-yl)amino]benzamide as a colorless oil. MS (ES), m/z 406 (MH$^+$). 300 MHz $^1$H NMR (CDCl$_3$) δ1.17 (t, J=7.0 Hz, 6H), 1.68-1.90 (m, 4H), 2.06 (br t, J=10.6 Hz, 2H), 2.91-3.08 (m, 4H), 3.31-3.52 (m, 4H), 3.75-3.92 (br m, 1H), 4.52 (s, 2H), 5.09-5.25 (m, 2H), 5.75-5.95 (m, 1H), 6.65 (d, J=8.7 Hz, 2H), 7.15-7.38 (m, 7H).

Example 6

N,N-Diethyl-4-[benzyl(1-isopropylpiperidin-4-yl) amino]benzamide (Compound 10)

To a solution of N,N-diethyl-4-[benzyl(piperidin-4-yl) amino]benzamide (Compound 8) (0.27 g, 0.739 mmole), acetone (0.09 g, 1.48 mmol), and acetic acid (0.04 g, 0.739 mmol) in 10 mL of dry dichloromethane was added sodium triacetoxyborohydride (0.31 g, 1.48 mmol) under nitrogen. The mixture was stirred for 40 hours, and then aqueous 1 N NaOH (20 mL) solution was added. After 1 h of stirring, the layers were separated, and the aqueous layer was extracted twice with dichloromethane (15 mL). The organic extracts were combined, washed twice with 1 N NaOH (20 mL), dried (Na$_2$SO$_4$), and concentrated to give a brown-black glass. This material was purified on a flash silica gel column (5% methanol-chloroform to 10% methanol-chloroform) to provide 0.13 g (43%) of N,N-diethyl-4-[benzyl(1-isopropylpiperidin-4-yl)amino]benzamide as a colorless oil. MS (ES), m/z 408 (MH$^+$). 300 MHz $^1$H NMR (CDCl$_3$) δ1.06 (d, J=6.4 Hz, 6H), 1.17 (t, J=7.0 Hz, 6H), 1.68-1.92 (m, 4H), 2.29 (br t, 2H), 2.69-2.85 (br m, 1H), 2.97 (br d, J=10.3 Hz, 2H), 3.32-3.52 (m, 4H), 3.74-3.89 (br m, 1H), 4.53 (s, 2H), 6.65 (d, J=8.8 Hz, 2H), 7.18-7.42 (m, 7H).

Example 7

N,N-Diethyl-4-[benzyl(1-methylpiperidin-4-yl) amino]benzamide (Compound 14)

(Takeda, M. et al. *Chem. Pharm. Bull.* 1992, 40, 1186)

To a solution of N,N-diethyl-4-[benzyl(piperidin-4-yl) amino]benzamide (Compound 8) (0.67 g, 0.207 mmole) in 10 mL of methanol was added 37% formalin solution (1 mL), and the resulting mixture was cooled in an ice bath under Argon. To this mixture was added sodium borohydride (0.69 g, 18.2 mmol) in small portions. The reaction mixture was allowed to warm to ambient temperature and was stirred for three days. The reaction mixture was diluted with water (25 mL), and the resulting solution was extracted three times with chloroform (25 mL). The organic extracts were combined, dried (Na$_2$SO$_4$), and concentrated to provide a pale yellow oil. This material was purified on a flash silica gel column (10% methanol-chloroform to 15% methanol-chloroform) to provide 0.54 g of N,N-diethyl-4-[benzyl(1-methylpiperidin-4-yl)amino]benzamide as a pale yellow semisolid. This material was dissolved in acetonitrile, and oxalic acid (0.13 g) was added. Upon addition of diethyl ether, a cream-colored precipitate came out of solution. Recrystallization from acetonitrile and diethyl ether afforded 0.18 g (18% yield) of a cream-colored solid, mp 101-105° C. MS (ES), m/z 380 (MH$^+$). 300 MHz $^1$H NMR (DMSO-d$_6$) δ0.85-1.15 (br m, 6H), 1.75-2.02 (br m, 2H), 2.72 (s, 3H), 2.95-3.15 (br m, 2H), 3.16-3.45 (m, 6H), 4.12-4.30 (br m, 1H), 4.49 (br s, 2H), 6.63-6.82 (br m, 2H), 7.10-7.40 (m, 7H). Elemental analysis: Calculated for C$_{24}$H$_{33}$N$_3$O.C$_2$H$_2$O$_4$.0.6H$_2$O: C, 65.01; H, 7.60; N, 8.75; H$_2$O, 2.25. Found C, 64.77; H, 7.25; N, 8.59; Karl Fischer H$_2$O, 1.55.

Example 8

N,N-Diethyl-4-[benzyl(1-[3-dimethylaminopropyl] piperidin-4-yl) amino]benzamide (Compound 11)

(Sessler, J. L.; Sibert, J. W. *Tetrahedron* 1993, 49, 8727)

To a solution of N,N-diethyl-4-[benzyl(piperidin-4-yl) amino]benzamide (Compound 8) (0.29 g, 0.793 mmole) in 25 mL of acetonitrile was added 3-(dimethylamino)propyl chloride hydrochloride (0.013 g, 0.793 mmol), sodium iodide (0.02 g, 0.119 mmol), and triethylamine (0.32 g, 3.18 mmol). The reaction mixture was refluxed for 20 hours under Argon and then was cooled and concentrated in vacuo. To the residue was added, aqueous sodium hydroxide (1 N) solution (30 mL), and the resulting solution was extracted three times with chloroform (25 mL). The organic extracts were combined, washed with sodium carbonate solution, dried (Na$_2$SO$_4$), and concentrated to provide a brown oil. This material was purified on a flash silica gel column (10% methanol-chloroform to 17.5% methanol-chloroform) to provide 0.09 g (25%) of N,N-diethyl-4-[benzyl(1-(3-dimethylaminopropyl)piperidin-4-yl)amino]benzamide as a pale rose glass. MS (ES), m/z 451 (MH$^+$). 300 MHz $^1$H NMR (CDCl$_3$) δ1.17 (t, J=7.0 Hz, 6H), 1.69-1.89 (m, 4H), 2.14 (br t, 2H), 2.18-2.38 (br m, 2H), 2.42 (s, 4H), 2.47 (t, J=7.1 Hz, 2H), 2.59 (t, J=6.9 Hz, 2H), 3.06 (br d, J=11.6 Hz, 2H), 3.30-3.49 (m, 4H), 3.72-3.90 (br m, 1H), 4.52 (s, 2H), 6.65 (d, J=8.7 Hz, 2H), 7.10-7.30 (m, 7H).

Example 9

N,N-Diethyl-3-[3-methoxyphenyl(1-propylpiperidin-4-yl)aminomethyl]benzamide (Compound 18)

To a solution of 1-propyl-4-piperidone (25.0 g, 177 mmol), 3-methoxyaniline (9.7 g, 177 mmol), and acetic acid (10.6 g, 177 mmol) in 500 mL of dry 1,2-dichloroethane was added sodium triacetoxyborohydride (56.3 g, 266 mmol) under nitrogen. The mixture was stirred for 19 h, and then aqueous 1 N NaOH (250 mL) solution was added. After 20 h of stirring, the layers were separated, and the aqueous layer was extracted twice with dichloromethane (100 mL). The organic extracts were combined and dried (Na$_2$SO$_4$), and concentrated to give 53.11 g of a yellow oil. This material was purified on flash silica gel (chloroform to 8% methanol-chloroform) to provide the acetate salt of the desired product as 29.7 g of a cream-colored solid. A portion of this material (28.3 g) was dissolved in chloroform (300 mL) and was washed three times with 1 N NaOH (100 mL), dried (Na$_2$SO$_4$), and concentrated to give 19.1 g of N-(3-methoxyphenyl)-1-propyl-4-piperidinamine as a light pink solid. MS (ES), m/z 249 (MH$^+$). 300 MHz $^1$H NMR (CDCl$_3$) δ0.89 (t, J=7.3 Hz, 3H), 1.38-1.59 (m, 4H), 1.99-2.15 (m, 4H), 2.25 (dd, J=9.1, 6.5 Hz, 2H), 2.87 (br d, J=11.8 Hz, 2H), 3.19-3.35 (br m, 1H), 3.54 (br d, J=8.1 Hz, 2H), 3.77 (s, 3H), 6.15 (t, J=2.1 Hz, 1H), 6.18-6.29 (m, 2H), 7.06 (t, J=8.1 Hz, 1H).

To a solution of 3-carboxybenzaldehyde (5.0 g, 33.3 mmol) in 50 mL of tetrahydrofuran was added carbonyl diimidazole (5.67 g, 35.0 mmol) under Argon. After 1 h of stirring, diethylamine (4.87 g, 66.7 mmol) was added, and the reaction mixture was stirred for 18 h and then refluxed one hour. After cooling, water (50 mL) was added to the reaction flask, and the contents were concentrated on a rotary evaporator. The resulting mixture was extracted three times with dichloromethane (50 mL). These extracts were combined, washed twice with 1 N aqueous hydrochloric acid solution (50 mL) and twice with water (50 mL), dried (Na$_2$SO$_4$), and concentrated to give a yellow oil. This material was purified on flash silica gel (1% methanol-chloroform to 3% methanol-chloroform) to provide 4.68 g (68% yield) of N,N-diethyl(3-formyl)benzamide as a light green oil. MS (ES), m/z 206 (MH$^+$). 300 MHz $^1$H NMR (CDCl$_3$) δ1.13 (br s, 3H), 1.27 (br s, 3H), 3.26 (br d, J=5.5 Hz, 2H), 3.58 (br d, J=5.5 Hz, 2H), 7.60 (t, J=7.6 Hz, 1H), 7.65 (t, J=7.8 Hz, 1H), 7.87-7.96 (m, 2H), 10.04 (s, 1H).

To a solution of N,N-diethyl(3-formyl)benzamide (1.24 g, 6.04 mmol) in 50 mL of 1,2-dichloroethane was added N-(3-methoxyphenyl)-1-propyl-4-piperidinamine (1.50 g, 6.04 mmol), acetic acid (0.36 g, 6.04 mmol), and sodium triacetoxyborohydride (1.92 g, 9.06 mmol). The reaction mixture was stirred for 1 h at ambient temperature and then was refluxed for 24 h. After the reaction mixture was cooled, 1 N NaOH (50 mL) was added. The mixture was stirred for 1 h, and then the layers were separated. The aqueous layer was extracted twice with dichloromethane (50 mL). The organic layers were combined and washed with 1N NaOH (75 mL) and dried (Na$_2$SO$_4$). Evaporation of the solvent afforded a red-orange oil. This material was purified on a flash silica gel column (3% methanol-chloroform to 10% methanol-chloroform) to provide 1.14 g of an orange-brown oil which appeared to be a mixture of desired product and the alcohol resulting from reduction of the aldehyde starting material. This material was taken up in diethyl ether (50 mL) and extracted three times with 1N HCl (50 mL). The acid extracts were combined and basified with solid Na$_2$CO$_3$, and then extracted three times with chloroform. The organic extracts were combined, dried (Na$_2$SO$_4$), and concentrated to provide 1.01 g of a golden brown oil which was still a mixture of the desired product and alcohol. This material was dissolved in ethyl acetate (50 mL) and extracted three times with 1N HCl (50 mL). The acid extracts were combined and basified with solid Na$_2$CO$_3$, and then extracted three times with chloroform. The organic extracts were combined, dried (Na$_2$SO$_4$), and concentrated to provide 0.45 g of a yellow-brown oil. This material was purified on a flash silica gel column (1% methanol-chloroform to 4% methanol-chloroform) to provide 0.15 g (6% yield) of N,N-diethyl-3-[3-methoxyphenyl (1-propylpiperidin-4-yl)aminomethyl]benzamide as a colorless oil. MS (ES), m/z 438 (MH$^+$). 300 MHz $^1$H NMR (DMSO-d$_6$) δ0.89 (t, J=7.3 Hz, 3H), 0.92-1.07 (br m, 3H), 1.12-1.32 (br m, 3H), 1.42-1.58 (m, 2H), 1.64-1.89 (m, 4H), 2.03 (br t, J=11.2 Hz, 2H), 2.29 (dd, J=7.8 Hz, 2H), 3.00 (br d, J=11.6 Hz, 2H), 3.07-3.25 (br m, 2H), 3.40-3.58 (br m, 2H), 3.71 (s, 3H), 3.72-3.82 (br m, 1H), 4.49 (s, 2H), 6.20-6.32 (m, 3H), 7.06 (t, J=8.2 Hz, 1H), 7.16-7.35 (m, 4H).

Using the procedure of Example 9 and the appropriate reagents, starting materials and purification methods known to those skilled in the art, other compounds of the present invention may be prepared including, but not limited to:

| Cpd | Name | ES-MS m/z (MH$^+$) |
|---|---|---|
| 17 | N,N-diethyl-4-[3-methoxyphenyl(1-propylpiperidin-4-yl)aminomethyl]benzamide | 438 |
| 19 | N,N-diethyl-3-[3-hydroxyphenyl(1-propylpiperidin-4-yl)aminomethyl]benzamide | 424 |

Example 10

N,N-Diethyl-3-[phenyl(1-propylpiperidin-4-yl)aminomethyl]benzamide (Compound 20)

To a solution of 3-(N-tert-butoxycarbonylmethylamino) benzoic acid (10.0 g, 39.8 mmol) in 100 mL of tetrahydrofuran was added carbonyl diimidazole (6.78 g, 41.8 mmol) under Argon. After 2 h of stirring, diethylamine (5.82 g, 79.4 mmol) was added, and the reaction mixture was stirred for 18 h and then refluxed 3 h. After cooling, water (50 mL) was added to the reaction flask, and the contents were concentrated on a rotary evaporator. The resulting mixture was extracted three times with dichloromethane (50 mL). These extracts were combined, washed twice with 1 N aqueous hydrochloric acid solution (50 mL) and twice with water (50 mL), dried (Na$_2$SO$_4$), and concentrated to give 11.9 g (98%) of N,N-diethyl 3-(N-tert-butoxycarbonylmethylamino)benzamide as a yellow oil. MS (ES), m/z 307 (MH$^+$). 300 MHz $^1$H NMR (CDCl$_3$) δ1.03-1.19 (br m, 3H), 1.15-1.30 (br m, 3H), 1.45 (s, 9H), 3.14-3.31 (br m, 2H), 3.45-3.62 (br m, 2H), 4.33 (d, J=5.6 Hz, 1H), 4.95 (br s, 1H), 7.19-7.38 (m, 4H).

To a solution of N,N-diethyl 3-(N-tert-butoxycarbonylmethylamino)benzamide (11.9 g, 38.8 mmol) in 550 mL of dichloromethane was added 200 mL of trifluoroacetic acid. After 20 h of stirring, the reaction mixture was diluted with 500 mL of dichloromethane. Then 1N NaOH solution (700 mL) was added slowly to the reaction mixture. The layers were separated, and the aqueous layer was extracted three times with dichloromethane (200 mL). The organic extracts were combined, washed with brine (500 mL), dried (Na$_2$SO$_4$), and concentrated to give 7.62 g (95%) of N,N-diethyl 3-aminomethylbenzamide as an orange oil. MS (ES), m/z 207 (MH$^+$). 300 MHz $^1$H NMR (CDCl$_3$) δ0.93-1.14 (br m, 3H), 1.15-1.36 (br m, 3H), 1.56 (s, 2H), 3.10-3.40 (br m, 2H), 3.42-3.62 (br m, 2H), 3.89 (s, 2H), 7.18-7.27 (m, 1H), 7.28-7.39 (m, 3H).

To a solution of 1-propyl-4-piperidone (5.20 g, 36.8 mmol), N,N-diethyl 3-aminomethylbenzamide (7.60 g, 36.8 mmol), and acetic acid (2.2 g, 36.8 mmol) in 100 mL of dry dichloromethane was added sodium triacetoxyborohydride (15.6 g, 73.7 mmol) under nitrogen. The mixture was stirred for three days, and then aqueous 1 N NaOH (100 mL) solution was added. After 1 h of stirring, the layers were separated, and the aqueous layer was extracted twice with dichloromethane (50 mL). The organic extracts were combined, washed with 1N NaOH (100 mL), and dried (Na$_2$SO$_4$), and concentrated to give a brown oil. This material was purified on flash silica gel (15% methanol-chloroform to 25% methanol-chloroform) to provide 8.38 g (69%) of N,N-diethyl-[3-(1-propylpiperidin-4-yl)aminomethyl]benzamide as a yellow oil. MS (ES), m/z 332 (MH$^+$). 300 MHz $^1$H NMR (CDCl$_3$) δ0.89 (t, J=7.3 Hz, 3H), 0.95-1.32 (m, 6H), 1.32-1.56 (m, 4H), 1.82-2.01 (m, 4H), 2.26 (dd, J=9.2, 6.7 Hz, 2H), 2.43-2.56 (m, 1H), 2.88 (br d, J=11.8 Hz, 2H), 3.13-3.44 (br d, 2H), 3.43-3.61 (br d, 2H), 3.84 (s, 2H), 7.17-7.38 (m, 4H).

A solution of N,N-diethyl-[3-(1-propylpiperidin-4-yl) aminomethyl]benzamide (3.22 g, 9.71 mmol), bromobenzene (1.53 g, 9.71 mmol), Pd$_2$dba$_3$ (0.09 g, 0.0971 mmol), (+)-BINAP (0.18 g, 0.291 mmol) and sodium t-butoxide 1.31 g, 13.6 mmol) in 14 mL of dry toluene was heated at 120° C. under Argon in a pressure vessel for 40 h. The mixture was cooled, and dichloromethane (75 mL) and water (75 mL) were added to the reaction flask. The layers were separated, and the aqueous layer was extracted twice with dichloromethane (75 mL). The organic layers were combined and washed with brine (75 mL) and dried (Na$_2$SO$_4$). Evaporation of the solvent afforded a dark brown oil with some solid particles evident. This material was purified on a flash silica gel column (5% methanol-chloroform to 10% methanol-chloroform) to provide 0.99 g (25% yield) of N,N-diethyl-3-[phenyl(1-propylpiperidin-4-yl)aminomethyl]benzamide as a golden-brown oil. This material was dissolved in dichloromethane, and oxalic acid (0.18 g) was added. Upon addition of diethyl ether, a cream-colored precipitate came out of solution. Recrystallization from dichloromethane and diethyl ether afforded 0.28 g (6% yield) of a cream-colored solid, mp 78-82° C. MS (ES), m/z 408 (MH$^+$). 300 MHz $^1$H NMR (DMSO-d$_6$) δ0.72-0.99 (br m, 6H), 1.00-1.30 (br m, 3H), 1.52-1.72 (m, 2H), 1.79-2.09 (m, 4H), 2.79-2.99 (br m, 2H), 2.98-3.05 (br m, 4H), 3.24-3.39 (br m, 2H), 3.38-3.62 (m, 2H), 4.08-4.29 (br m, 1H), 4.47 (br s, 2H), 6.65 (t, J=7.0 Hz, 1H), 6.76 (d, J=8.0 Hz, 2H), 6.93-7.25 (m, 4H), 7.25-7.45 (m, 2H). Elemental analysis: Calculated for C$_{26}$H$_{37}$N$_3$O.C$_2$H$_2$O$_4$.0.6H$_2$O: C, 66.14; H, 7.97; N, 8.26; H$_2$O, 0.60. Found C, 66.19; H, 7.62; N, 8.11; Karl Fischer H$_2$O, 0.59.

Using the procedure of Example 10 and the appropriate reagents, starting materials and purification methods known to those skilled in the art, other compounds of the present invention may be prepared including, but not limited to:

| Cpd | Name | ES-MS m/z (MH$^+$) |
|---|---|---|
| 21 | N,N-diethyl-3-[3-fluorophenyl(1-propylpiperidin-4-yl)aminomethyl]benzamide | 426 |

BIOLOGICAL EXAMPLES

δ-opioid and μ-opioid receptor binding for the compounds of the present invention were determined according to the following procedures and the indicated results were obtained.

Example 1

Rat Brain δ-Opioid Receptor Binding Assay

The activity of the compounds of the invention as analgesics was demonstrated by the rat brain δ-opioid receptor binding assay as described below.

Procedure

Male, Wistar rats (150-250 g, VAF, Charles River, Kingston, N.Y.) are killed by cervical dislocation, and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the δ-opioid binding assays. Following incubation with the δ-selective peptide ligand [$^3$H]DPDPE at 25° C., the tube contents are filtered through Whatman GF/B filter sheets on a Brandel cell harvester. The tubes and filters are rinsed three times with 4 mL of 10 mM HEPES (pH 7.4), and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a K$_i$ value (when a range of concentrations are tested).

% Inhibition was calculated as:

$$1 - \left( \frac{\text{test compound dpm} - \text{nonspecific dpm}}{\text{total dpm} - \text{nonspecific dpm}} \right) \times 100\%;$$

K$_i$ value is calculated using the LIGAND (Munson, P. J. and Rodbard, D., Anal. Biochem. 107: 220-239, 1980) data analysis program. Those compounds with K$_i$ values of >10000 nM are considered to be biologically inactive.

Table 4 shows the biological activity in % inhibition or Ki values for instant compounds as measured in the rat brain δ-opioid receptor binding assay.

TABLE 4

δ-Opioid Receptor Binding (K$_i$ nM or % Inhibition)

| Cpd | K$_i$ nM or % Inhibition @ 1 μM |
|---|---|
| 1 | 240 |
| 2 | 14.6 |
| 3 | 50.4 |
| 4 | 17% |
| 5 | 3468 |
| 6 | 71.8 |
| 7 | 26.2 |
| 8 | 71.1 |
| 9 | 73 |
| 10 | 585 |
| 11 | 1770 |
| 12 | 11.4 |
| 13 | 599 |
| 14 | 109 |
| 15 | 2192 |
| 16 | 110 |
| 17 | 5% |
| 18 | 3990 |
| 19 | 356 |
| 20 | 1050 |
| 21 | 1030 |

Example 2

Rat Brain μ-Opioid Receptor Binding Assay

The activity of compounds of the invention as analgesics is demonstrated by the rat brain μ-opioid receptor binding assay as described below.

Procedure

Male, Wistar rats (150-250 g, VAF, Charles River, Kingston, N.Y.) are killed by cervical dislocation and their brains removed and placed immediately in ice cold Tris HCl buffer (50 mM, pH 7.4). The forebrains are separated from the remainder of the brain by a coronal transection, beginning dorsally at the colliculi and passing ventrally through the midbrain-pontine junction. After dissection, the forebrains are homogenized in Tris buffer in a Teflon®-glass homogenizer. The homogenate is diluted to a concentration of 1 g of forebrain tissue per 100 mL Tris buffer and centrifuged at 39,000×G for 10 min. The pellet is resuspended in the same volume of Tris buffer with several brief pulses from a Polytron homogenizer. This particulate preparation is used for the μ-opioid binding assays. Following incubation with the μ-selective peptide ligand [$^3$H]DAMGO at 25° C., the tube contents are filtered through Whatman GF/B filter sheets on a Brandel cell harvester. The tubes and filters are rinsed three times with 4 mL of 10 mM HEPES (pH 7.4) and the radioactivity associated with the filter circles determined using Formula 989 scintillation fluid (New England Nuclear, Boston, Mass.) in a scintillation counter.

Analysis

The data are used to calculate either the % inhibition compared to control binding (when only a single concentration of test compound is evaluated) or a $K_i$ value (when a range of concentrations is tested).

% Inhibition is calculated as:

$$1 - \left( \frac{\text{test compound dpm} - \text{nonspecific dpm}}{\text{total dpm} - \text{nonspecific dpm}} \right) \times 100\%;$$

$K_i$ value is calculated using the LIGAND (Munson, P. J. and Rodbard, D., Anal. Biochem. 107: 220-239, 1980) data analysis program. Those compounds with $K_i$ values of >10000 nM are considered to be biologically inactive.

Table 5 shows the biological activity in Ki values for instant compounds as measured in the rat brain μ-opioid receptor binding assay.

TABLE 5

μ-Opioid Receptor Binding ($K_i$ nM)

| Cpd | $K_i$ nM |
| --- | --- |
| 1 | 9283 |
| 2 | 640 |
| 3 | 2140 |
| 4 | NA |
| 5 | 10000 |
| 6 | 1380 |
| 7 | 901 |
| 8 | 10000 |
| 9 | 10000 |
| 10 | 3790 |
| 11 | 10000 |
| 12 | 10000 |
| 13 | NA |
| 14 | NA |
| 15 | 10000 |
| 16 | NA |
| 17 | NA |
| 18 | 10000 |
| 19 | 155 |
| 20 | NA |
| 21 | NA |

Example 3

Mouse Acetylcholine Bromide-Induced Abdominal Constriction Assay

The activity of compounds of the invention as analgesics was further demonstrated by the mouse acetylcholine bromide-induced abdominal constriction assay as described below.

Procedure

The mouse acetylcholine-induced abdominal constriction assay, as described by Collier et al. in *Brit. J. Pharmacol. Chem. Ther.*, 32: 295-310, 1968 with minor modifications, was used to assess analgesic potency of the compounds of formula (I). The test drugs or appropriate vehicles were administered orally (p.o.) and 30 min later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten min observation period for the occurrence of an abdominal constriction response (defined as a wave of constriction and elongation passing caudally along the abdominal wall, accompanied by a twisting of the trunk and followed by extension of the hind limbs). For compounds of the present invention, the percent inhibition of this response to a nociceptive stimulus (equated to % analgesia) was calculated as follows:

$$\% \text{ Inhibition} = \left( \frac{\text{No. of CAR} - \text{No. of DTAR}}{\text{No. of CAR}} \right) \times 100\%$$

CAR: Control Animal Responses

DTAR: Drug-Treated Animal Responses

Table 6 shows the biological activity in % inhibition at a dose of 150 μmole/Kg p.o. for instant compounds as measured in the mouse acetylcholine bromide-induced abdominal constriction (MAIT) assay.

TABLE 6

MAIT (% Inhibition)

| Cpd | % Inhibition @150 μmol/kg |
| --- | --- |
| 2 | 13.3 |
| 6 | 100 |
| 7 | 100 |
| 8 | 33.3 |
| 9 | 84.6 |
| 12 | 0 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

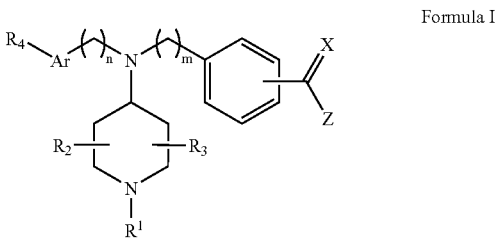

Formula I wherein:

Ar is aryl;

m is an integer from 0 to 2, n is an integer from 0 to 2, with the proviso that m and n are not both simultaneously 0;

$R_1$ is selected from the group consisting of hydrogen, $C_{1-8}$alkyl, $C_{2-8}$alkenyl, aryl, aryl($C_{1-8}$)alkyl, amino($C_{1-8}$)alkyl, $C_{1-8}$alkyl-NH—($C_{1-8}$)alkyl, ($C_{1-8}$alkyl)$_2$—N—($C_{1-8}$)alkyl, hydroxy($C_{1-8}$)alkyl and $C_{1-8}$alkoxy($C_{1-8}$)alkyl;

$R_2$ and $R_3$ are optionally present and independently selected from $C_{1-8}$alkyl;

$R_4$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkyloxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —S(O$_2$)NH$_2$, —S(O$_2$)NH($C_{1-8}$)alkyl, —S(O$_2$)N[($C_{1-8}$)alkyl]$_2$, —C(O)($C_{1-8}$)alkyl, —C(O)aryl, —C(O)($C_{1-8}$)alkylaryl, aryl, halogen, hydroxy, cyano, and nitro;

X is selected from the group consisting of O and S;

Z is N($R_5$)($R_6$);

$R_5$ and $R_6$ are independently selected from the group consisting of hydrogen, $C_{1-8}$alkyl, hydroxy($C_{1-8}$)alkyl, $C_{2-8}$alkenyl, $C_{3-8}$cycloalkyl, aryl and aryl($C_{1-8}$)alkyl, wherein said cycloalkyl, aryl and the aryl portion of aryl($C_{1-8}$)alkyl are optionally substituted with one to three substituents independently selected from the group consisting of $C_{1-8}$alkyl, $C_{2-8}$alkenyl, $C_{1-8}$alkoxy, trifluoro($C_{1-8}$)alkyl, trifluoro($C_{1-8}$)alkoxy, $C_{3-8}$cycloalkyl and halogen; and, the moiety —C(X)Z is attached on the phenyl at the 3 or 4 position;

and pharmaceutically acceptable enantiomers, diastereomers and salts thereof.

2. The compound of claim 1 wherein Ar is phenyl or naphthyl.

3. The compound of claim 1 wherein Ar is phenyl.

4. The compound of claim 1 wherein m is an integer from 0 to 1, n is an integer from 0 to 1, with the proviso that m and n are not both simultaneously 0.

5. The compound of claim 1 wherein $R_1$ is selected from the group consisting of hydrogen, $C_{1-4}$alkyl, $C_{2-4}$alkenyl, aryl, aryl($C_{1-4}$)alkyl, NH$_2$($C_{1-4}$)alkyl, $C_{1-4}$alkyl-NH—($C_{1-4}$)alkyl, ($C_{1-4}$alkyl)$_2$—N—($C_{1-4}$)alkyl, hydroxy($C_{1-4}$)alkyl and $C_{1-4}$alkoxy($C_{1-4}$)alkyl.

6. The compound of claim 1 wherein $R_1$ is selected from the group consisting of hydrogen, $C_{1-4}$alkyl and $C_{2-4}$alkenyl.

7. The compound of claim 1 wherein $R_1$ is selected from the group consisting of hydrogen, n-propyl and allyl.

8. The compound of claim 1 wherein $R_2$ and $R_3$ are optionally present and independently selected from $C_{1-4}$alkyl.

9. The compound of claim 1 wherein $R_2$ and $R_3$ are not present.

10. The compound of claim 1 wherein $R_4$ is one to three substituents.

11. The compound of claim 1 wherein $R_4$ is independently selected from the group consisting of hydrogen, $C_{1-8}$alkyl, $C_{1-8}$alkoxy, trifluoro($C_{1-8}$)alkyl, trifluoro($C_{1-8}$)alkoxy, cyano, halogen, hydroxy and nitro.

12. The compound of claim 1 wherein $R_4$ is independently selected from the group consisting of hydrogen, $C_{1-8}$alkoxy, trifluoro($C_{1-8}$)alkyl, hydroxy and halogen.

13. The compound of claim 1 wherein $R_4$ is independently selected from the group consisting of hydrogen, methoxy, trifluoromethyl, hydroxy, fluoro and chloro.

14. The compound of claim 1 wherein X is O.

15. The compound of claim 1 wherein $R_5$ and $R_6$ are independently selected from the group consisting of hydrogen, $C_{1-4}$alkyl, hydroxy($C_{1-4}$)alkyl, $C_{2-4}$alkenyl, $C_{3-8}$cycloalkyl, aryl and aryl($C_{1-4}$)alkyl, wherein said cycloalkyl, aryl and the aryl portion of aryl($C_{1-8}$)alkyl are optionally substituted with one to three substituents independently selected from the group consisting of $C_{1-4}$alkyl, $C_{2-4}$alkenyl, $C_{1-4}$alkoxy, $C_{3-8}$cycloalkyl, halogen, trifluoro($C_{1-4}$)alkyl and trifluoro($C_{1-4}$)alkoxy.

16. The compound of claim 1 wherein $R_5$ and $R_6$ are independently selected from the group consisting of hydrogen and $C_{1-4}$alkyl.

17. The compound of claim 1 wherein $R_5$ and $R_6$ independently selected from the group consisting of hydrogen, methyl and ethyl.

18. The compound of claim 1 wherein the compound of Formula (I) is selected from Formula (Ia):

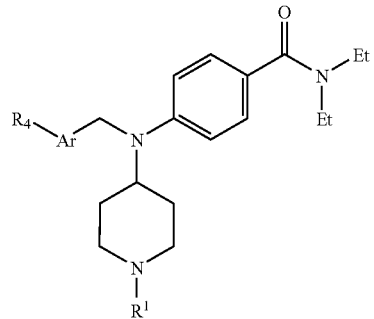

wherein

Ar is aryl;

$R_1$ is selected from the group consisting of hydrogen, $C_{1-8}$alkyl, $C_{2-8}$alkenyl, aryl, aryl($C_{1-8}$)alkyl, amino($C_{1-8}$)alkyl, $C_{1-8}$alkyl-NH—($C_{1-8}$)alkyl, ($C_{1-8}$alkyl)$_2$—N—($C_{1-8}$)alkyl, hydroxy($C_{1-8}$)alkyl and $C_{1-8}$alkoxy($C_{1-8}$)alkyl;

$R_4$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkyloxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkylaryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$)alkyl]$_2$, —NHC(O)($C_{1-8}$)alkyl, —SO$_2$H, —SO$_2$($C_{1-8}$)alkyl, —S(O$_2$)NH$_2$, —S(O$_2$)NH($C_{1-8}$)alkyl, —S(O$_2$)N[($C_{1-8}$)alkyl]$_2$, —C(O)($C_{1-8}$)alkyl, —C(O)aryl, —C(O)($C_{1-8}$)alkylaryl, aryl, halogen, hydroxy, cyano, and nitro;

and pharmaceutically acceptable enantiomers, diastereomers and salts thereof.

19. The compound of claim 1 wherein the compound of Formula (I) is selected from Formula (Ia):

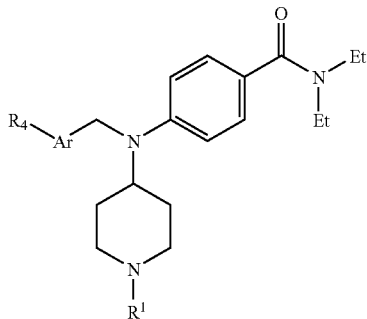

Wherein Ar, $R_1$ and $R_4$ are dependently selected from:

| $R_1$ | Ar | $R_4$ |
|---|---|---|
| n-Pr | phenyl | 3-methoxy |
| n-Pr | phenyl | 3-hydroxy |
| n-Pr | phenyl | 3-chloro |
| n-Pr | phenyl | 2-methoxy |
| n-Pr | phenyl | 2-hydroxy |
| n-Pr | phenyl | 3-fluoro |
| n-Pr | phenyl | H |
| H | phenyl | H |
| allyl | phenyl | H |
| i-Pr | phenyl | H |
| N,N-dimethyl aminopropyl | phenyl | H |
| n-Pr | phenyl | 4-methoxy |
| Me | phenyl | H |
| n-Pr | phenyl | 3-trifluoromethyl |
| n-Pr | phenyl | 4-fluoro | and pharmaceutically acceptable salts thereof.

20. The compound of claim 1 wherein the compound of Formula (I) is selected from Formula (Ib):

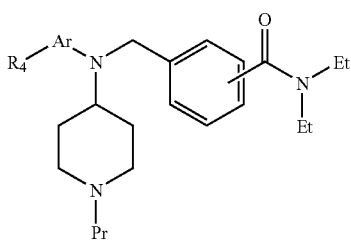

wherein
   Ar is aryl;
   $R_4$ is one to three substituents independently selected from the group consisting of hydrogen, $C_{1-8}$alkyl, $C_{2-8}$alkenyl, $C_{2-8}$alkynyl, $C_{3-8}$cycloalkyl, aryl($C_{1-8}$)alkyl, $C_{1-8}$alkoxy, aryloxy, aryl($C_{1-8}$)alkyloxy, $C_{1-8}$alkylthio, trifluoro($C_{1-8}$)alkyl, trifluoro($C_{1-8}$)alkoxy, amino, —NH($C_{1-8}$)alkyl, —N[($C_{1-8}$)alkyl]$_2$, —NH(aryl), —N(aryl)$_2$, —NH($C_{1-8}$)alkylaryl, —N[($C_{1-8}$)alkyl aryl]$_2$, —CO$_2$H, —CO$_2$($C_{1-8}$)alkyl, —CO$_2$(aryl), —C(O)NH$_2$, —C(O)NH($C_{1-8}$)alkyl, —C(O)N[($C_{1-8}$) alkyl]$_2$, —NHC(O)($C_{1-8}$)alkyl, —SO$_2$H, —SO$_2$($C_{1-8}$) alkyl, —S(O$_2$)NH$_2$, —S(O$_2$)NH($C_{1-8}$)alkyl, —S(O$_2$)N [($C_{1-8}$)alkyl]$_2$, —C(O)($C_{1-8}$)alkyl, —C(O)aryl, —C(O) ($C_{1-8}$)alkylaryl, aryl, halogen, hydroxy, cyano, and nitro;
   the moiety —C(X)Z is attached on the phenyl at the 3 or 4 position;
and pharmaceutically acceptable enantiomers, diastereomers and salts thereof.

21. The compound of claim 1 wherein the compound of Formula (I) is selected from Formula (Ib):

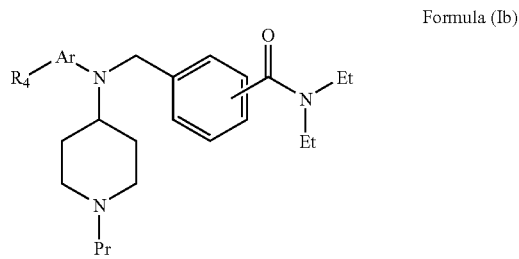

Wherein Ar, $R_4$ and the position for —C(O)(NEt$_2$) is selected from:

| Ar | $R_4$ | Amide Substitution |
|---|---|---|
| phenyl | 3-methoxy | 4 |
| phenyl | 3-methoxy | 3 |
| phenyl | 3-hydroxy | 3 |
| phenyl | H | 3 |
| phenyl | 3-fluoro | 3 | and pharmaceutically acceptable salts thereof.

22. A pharmaceutical composition comprising a compound of claim 1 and a pharmaceutically acceptable carrier.

* * * * *